United States Patent
Tornier et al.

(10) Patent No.: US 9,247,974 B2
(45) Date of Patent: Feb. 2, 2016

(54) POLYAXIAL SCREW WITH MECHANICAL THREAD AND ITS FRICTION DEVICE

(71) Applicant: CLARIANCE, Dainville (FR)

(72) Inventors: Alain Tornier, Saint Ismier (FR); Guy Viart, Saint Leger (FR); Jean Yves Leroy, Campagne-les-Hesdin (FR); Bruno Sauvage, Frevin Capelle (FR)

(73) Assignee: CLARIANCE, Dainville (FR)

( * ) Notice: Subject to any disclaimer, the term of this patent is extended or adjusted under 35 U.S.C. 154(b) by 129 days.

(21) Appl. No.: 13/936,348

(22) Filed: Jul. 8, 2013

(65) Prior Publication Data
US 2014/0012333 A1 Jan. 9, 2014

Related U.S. Application Data

(60) Provisional application No. 61/668,677, filed on Jul. 6, 2012.

(51) Int. Cl.
*A61B 17/70* (2006.01)
*A61B 17/86* (2006.01)

(52) U.S. Cl.
CPC .......... *A61B 17/8605* (2013.01); *A61B 17/7035* (2013.01); *A61B 17/7037* (2013.01); *A61B 17/7041* (2013.01); *A61B 17/8615* (2013.01)

(58) Field of Classification Search
CPC .................................................. A61B 17/7037
USPC .......................................................... 606/266
See application file for complete search history.

(56) References Cited

U.S. PATENT DOCUMENTS

| | | | |
|---|---|---|---|
| 7,862,588 B2* | 1/2011 | Abdou ........................ 606/246 |
| 7,927,359 B2* | 4/2011 | Trautwein et al. ............ 606/264 |
| 2003/0163133 A1* | 8/2003 | Altarac et al. .................. 606/61 |
| 2004/0006342 A1* | 1/2004 | Altarac et al. .................. 606/61 |
| 2005/0113927 A1* | 5/2005 | Malek ........................ 623/17.16 |
| 2006/0052786 A1* | 3/2006 | Dant et al. ....................... 606/61 |
| 2006/0229606 A1* | 10/2006 | Clement et al. ................. 606/61 |
| 2007/0055236 A1* | 3/2007 | Hudgins et al. ................. 606/61 |
| 2007/0093832 A1* | 4/2007 | Abdelgany ...................... 606/61 |
| 2007/0168036 A1* | 7/2007 | Ainsworth et al. ......... 623/17.13 |
| 2008/0119858 A1* | 5/2008 | Potash ............................ 606/73 |
| 2011/0054545 A1* | 3/2011 | Champagne et al. .......... 606/301 |
| 2011/0224738 A1* | 9/2011 | Sucec et al. ................... 606/315 |
| 2013/0184759 A1* | 7/2013 | Rinehart et al. .............. 606/266 |
| 2014/0114358 A1* | 4/2014 | Brumfield ..................... 606/266 |

* cited by examiner

*Primary Examiner* — David Bates
(74) *Attorney, Agent, or Firm* — Young & Thompson

(57) ABSTRACT

Disclosed is a polyaxial screw including a friction element (12) positioned between the head (3) of the threaded bone anchoring portion (2) and the head (9) of the mechanical thread anchoring portion (4) on the one hand, and a retaining element (13, 18) ensuring that the anchoring portions (2, 4) cannot separate from each other while guaranteeing that the anchoring portion with the mechanical thread (4) is free to move in vertical translation and angular pivoting with respect to the threaded bone anchoring portion (2) so as to be able to axially preposition the mechanical thread anchoring portion (4) with respect to the axial anchoring position of the threaded bone anchoring portion (2).

15 Claims, 7 Drawing Sheets

POLYAXIAL SCREW WITH MECHANICAL THREAD AND ITS FRICTION DEVICE

FIELD OF THE INVENTION

The present invention relates to a polyaxial screw including, between its threaded bone anchoring portion and its mechanical thread anchoring portion, a friction device and a retaining device ensuring axial pre-positioning of said portions with respect to one another.

BACKGROUND OF THE INVENTION

Polyaxial screws are known that include a threaded bone anchoring portion connected to an anchoring portion with a mechanical thread that is completely free in rotation around said threaded bone anchoring portion.

This freedom of movement of the mechanical thread anchoring portion with respect to the threaded bone anchoring portion is a source of some drawbacks when said screw is anchored in the vertebral body of a vertebra.

In fact, the mechanical thread anchoring portion is free from any pivoting around the threaded bone anchoring portion during the placement of the linking connector and the link rod by the surgeon.

This freedom of movement of the mechanical thread anchoring portion does not make it possible to position and keep the latter in a predetermined axial plane so the surgeon can mount the linking connector and the link rod.

The latter is required to keep the mechanical thread anchoring portion in a predetermined angular position with respect to the threaded bone anchoring portion fixed in the body of a vertebra during the placement of the linking connector and the link rod, making the mounting of the spinal device much more complicated.

SUMMARY OF THE INVENTION

The polyaxial screw according to the present invention aims to resolve these drawbacks by proposing, between the mechanical thread anchoring portion and the threaded bone anchoring portion, friction and retaining means ensuring the axial pre-positioning of said anchoring portions.

The polyaxial screw according to the present invention includes a threaded bone anchoring portion and an anchoring portion with a mechanical thread that are respectively provided with a head connected between them by retaining means, friction means positioned between the head of the threaded bone anchoring portion and the head of the mechanical thread anchoring portion, said retaining means ensuring that the anchoring portions cannot separate from each other while guaranteeing that the anchoring portion with the mechanical thread is free to move in vertical translation and angular pivoting with respect to said threaded bone anchoring portion so as to be able to axially pre-position said mechanical thread anchoring portion with respect to the axial anchoring position of the threaded bone anchoring portion.

The polyaxial screw according to the present invention includes friction means that are made up of a spiral wire in the form of a spring positioned inside a housing formed in the head of the threaded bone anchoring portion and on which the head with a spherical outer profile of the mechanical thread anchoring portion bears.

The polyaxial screw according to the present invention includes retaining means that are made up of two half-shells housed inside a slot formed in the head of the threaded bone anchoring portion.

The polyaxial screw according to the present invention includes two half-shells whereof the inner profile has a shape complementary to the outer profile of the spherical head of the mechanical thread anchoring portion.

The polyaxial screw according to the present invention includes a mechanical thread anchoring portion that is sectile.

The polyaxial screw according to the present invention includes a mechanical thread anchoring portion comprising a cavity for inserting a tool across from the spherical head.

The polyaxial screw according to the present invention includes friction means that are made up of a spiral wire in the form of a spring made from a material with a high friction coefficient, such as an alloy of titanium or cobalt.

The polyaxial screw according to the present invention includes a housing formed inside the head of the threaded bone anchoring portion that has a spherical profile.

The polyaxial screw according to the present invention includes a threaded bone anchoring portion whereof the head has, on its outer face, cavities making it possible to place a tool to rotate said threaded bone anchoring portion.

The polyaxial screw according to the present invention includes a threaded bone anchoring portion whereof the head has, on the outer face thereof, a thread making it possible to place retaining means ensuring that the anchoring portions cannot separate from each other while guaranteeing that the mechanical thread anchoring portion is free to move in vertical translation and angular pivoting with respect to said threaded bone anchoring portion.

The polyaxial screw according to the present invention includes a housing formed inside the head of the threaded bone anchoring portion comprising a cylindrical cavity in the middle thereof that is provided to receive one of the ends of the spring-shaped spiral wire of the friction means.

The polyaxial screw according to the present invention includes an anchoring portion with a mechanical thread, whereof the head comprises a cylindrical cavity in the middle thereof that is provided to receive one of the ends of the spring-shaped spiral wire of the friction means.

The polyaxial screw according to the present invention includes retaining means that are made up of a nut including a spherical inner face cooperating with the spherical outer profile of the head of the mechanical thread anchoring portion and a spherical outer face making it possible to receive a linking connector of a spinal fastening device.

BRIEF DESCRIPTION OF THE DRAWINGS

The following description in light of the appended drawings, which are provided as non-limiting examples, will make it possible to better understand the invention as well as the features and advantages thereof.

DETAILED DESCRIPTION OF THE INVENTION

Figure 1:
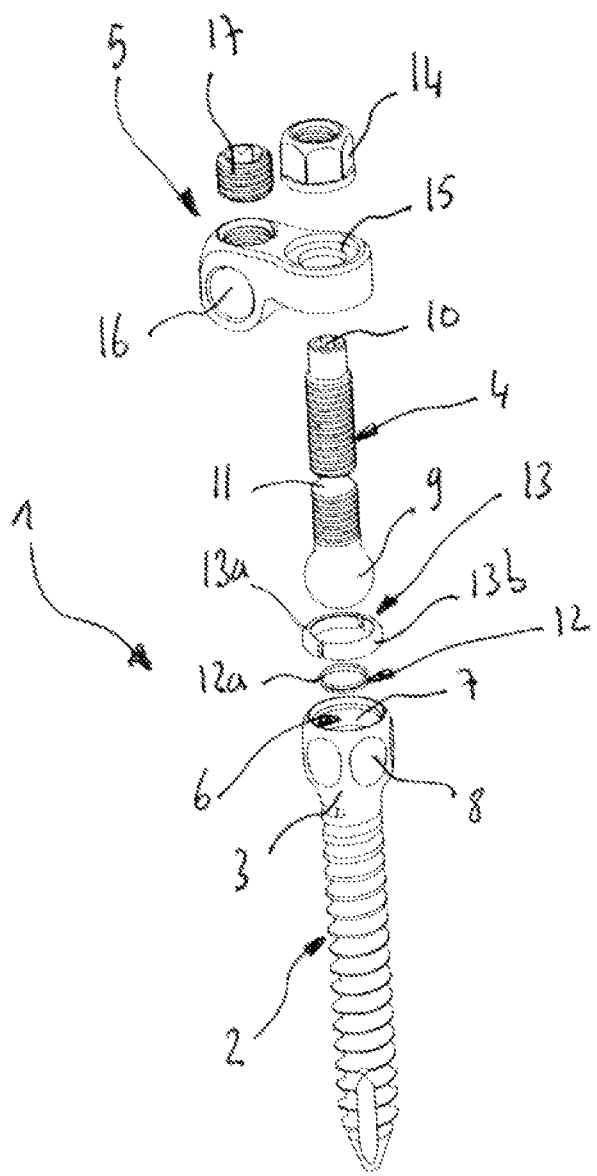
FIG. 1 is an exploded perspective view illustrating a polyaxial screw with a mechanical thread according to the present invention.
Figure 2:
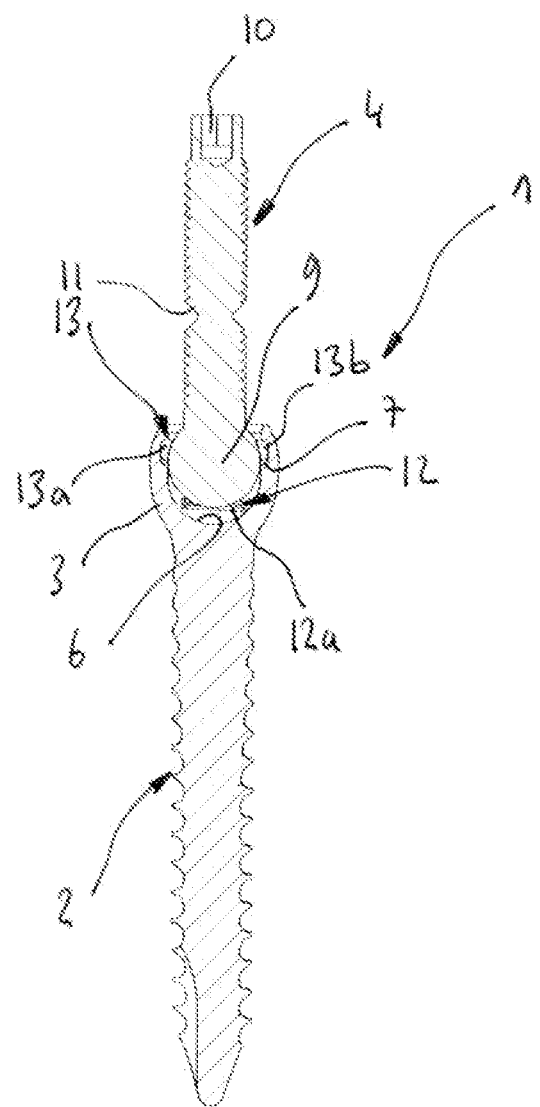
FIGS. 2 and 3 are cross-sectional views showing the mechanical thread polyaxial screw according to the present invention in different axial positions.
Figure 3:
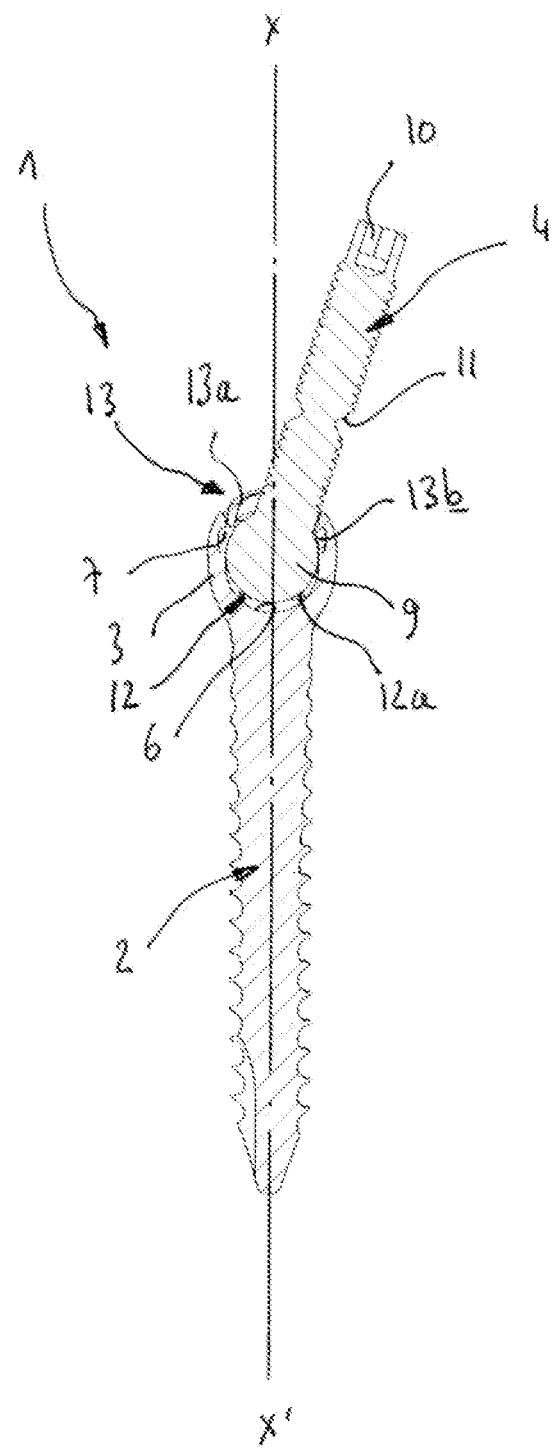

FIGS. 1 to 3 show a polyaxial screw 1 including a threaded bone anchoring portion 2 and an anchoring portion with a mechanical thread 4 respectively provided with a head 3 and 9 connected to each other by retaining means 13 ensuring that the mechanical thread anchoring portion 4 has a predetermined angular position so as to be able to immobilize a linking connector 5 of a spinal fastening device thereon.

An inner housing 6 with a spherical profile and a peripheral slot 7 is formed inside the head 3 of the threaded bone anchoring portion 2.

The head 3 has cavities 8 on its outer face making it possible to place a tool (not shown) to rotate the threaded bone anchoring portion 2 of the polyaxial screw 1.

The mechanical thread anchoring portion 4 is secured at one end thereof to a head 9 with a spherical outer profile, while the opposite end is pierced in the middle thereof with a cavity 10 for inserting a tool (not shown).

Between the spherical head 9 and its free end, the mechanical thread anchoring portion 4 of the polyaxial screw 1 includes at least one slot 11 providing a rupture area of said mechanical thread anchoring portion 4 so that the latter is sectile under a predetermined rotation effect.

The polyaxial screw 1 includes friction means 12 positioned inside the head 3 of the threaded bone anchoring portion 2 and on which the spherical head 9 of the mechanical thread bone anchoring portion 4 bears so as to be able to axially pre-position said anchoring portion with the mechanical thread 4 with respect to the axial anchoring position of the threaded bone anchoring portion 2 of the polyaxial screw 1 in the vertebral body of a vertebra.

The polyaxial screw 1 also includes retaining means 13 making it possible to prevent the spherical head 9 of the mechanical thread anchoring portion 4 from leaving the inner housing 6 of the head 3 of the threaded bone anchoring portion 2 when the two anchoring portions 2 and 4 are assembled.

The friction means 12 are made up of a spiral wire 12a in the form of a spring positioned inside the head 3 and more particularly in the bottom of the housing 6 of the threaded bone anchoring portion 2 and on which the spherical head 9 of the mechanical thread anchoring portion 4 bears.

The spiral wire 12a may be made from a material with a high friction coefficient, for example such as a titanium or cobalt alloy.

The retaining means 13 are made up of two half-shells 13a and 13b housed in the slot 7 formed inside the housing 6 of the head 3 of the threaded bone anchoring portion 2.

FIG. 3 shows the placement of the half-shell 13a inside the slot 7, with the understanding that the other half-shell 13b is inserted in the same way.

In fact, the half-shell 13a is inserted inside the slot 7 when the mechanical thread anchoring portion 4 is positioned in an inclined direction oriented toward the right with respect to the main and vertical axis xx' of the threaded bone anchoring portion 2.

Conversely, the other half-shell 13b is inserted in the same way when the anchoring portion with the mechanical thread 4 is positioned in an inclined direction oriented toward the left with respect to the main and vertical axis xx' of the threaded bone anchoring portion 2.

Each position of the mechanical thread anchoring portion 4 inclined to the right or left with respect to the threaded bone anchoring portion 2 makes it possible to free access to the slot 7 formed inside the housing 6 of the head 3 to insert two half-shells 13a and 13b.

When the two half-shells 13a and 13b are housed inside the slot 7, they make it possible to ensure that the anchoring portions 2 and 4 cannot separate while guaranteeing that the mechanical thread anchoring portion 4 is free to move in vertical translation and angular pivoting with respect to the threaded bone anchoring portion 2 implanted in the vertebral body of a vertebra.

The friction means 12 made up of a spring-shaped spiral wire 12a make it possible to keep the spherical head 9 of the anchoring portion with the mechanical thread 4 against the two half-shells 13a and 13b of the retaining means 13, the inner profile of which has a shape complementary to the outer shape of said spherical head 9.

The friction means 12 make it possible to keep the mechanical thread anchoring portion 4 in an axial position determined by the surgeon with respect to the threaded bone anchoring portion 2 during the assembly of the linking connector 5 and before it is immobilized in rotation by means of a tightening nut 14.

Figure 4:
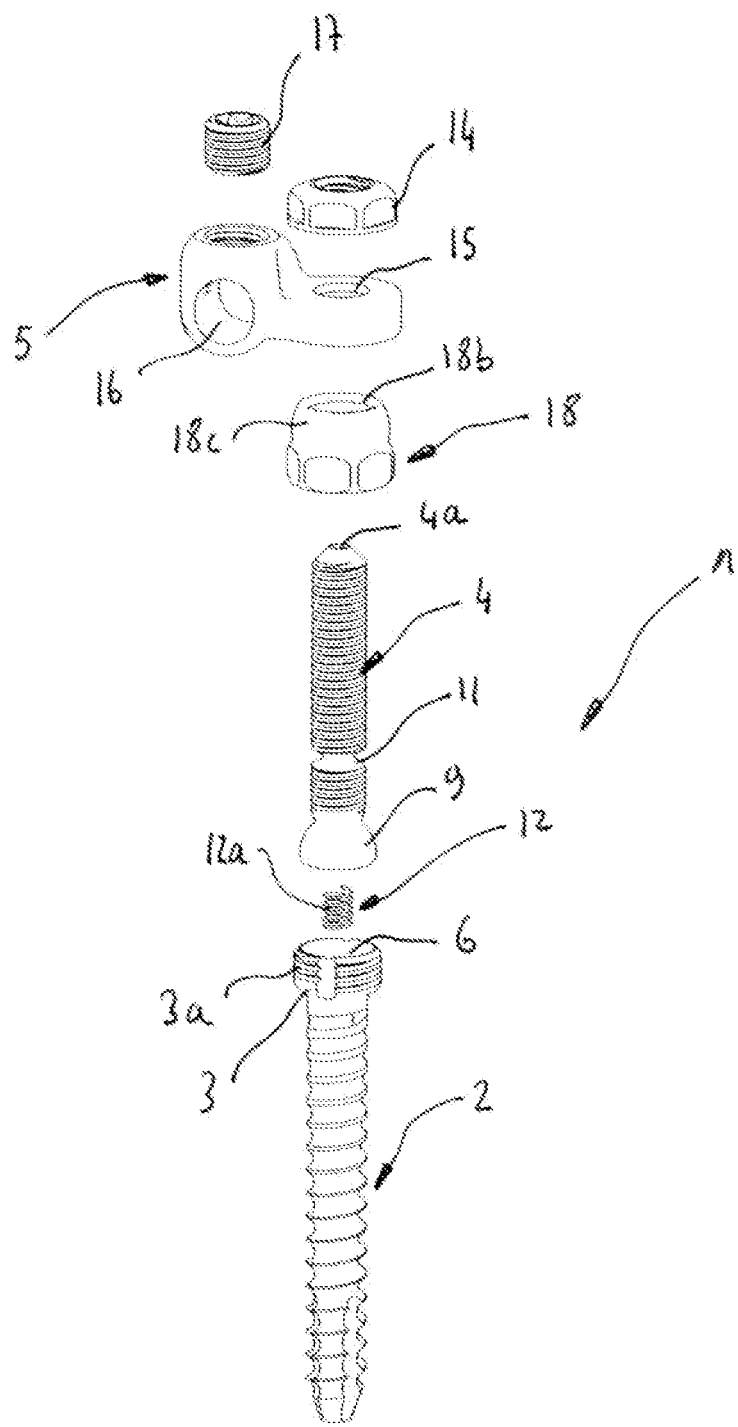
FIGS. 4 to 6 are views showing an alternative embodiment of the mechanical thread polyaxial screw according to the present invention.
Figure 5:
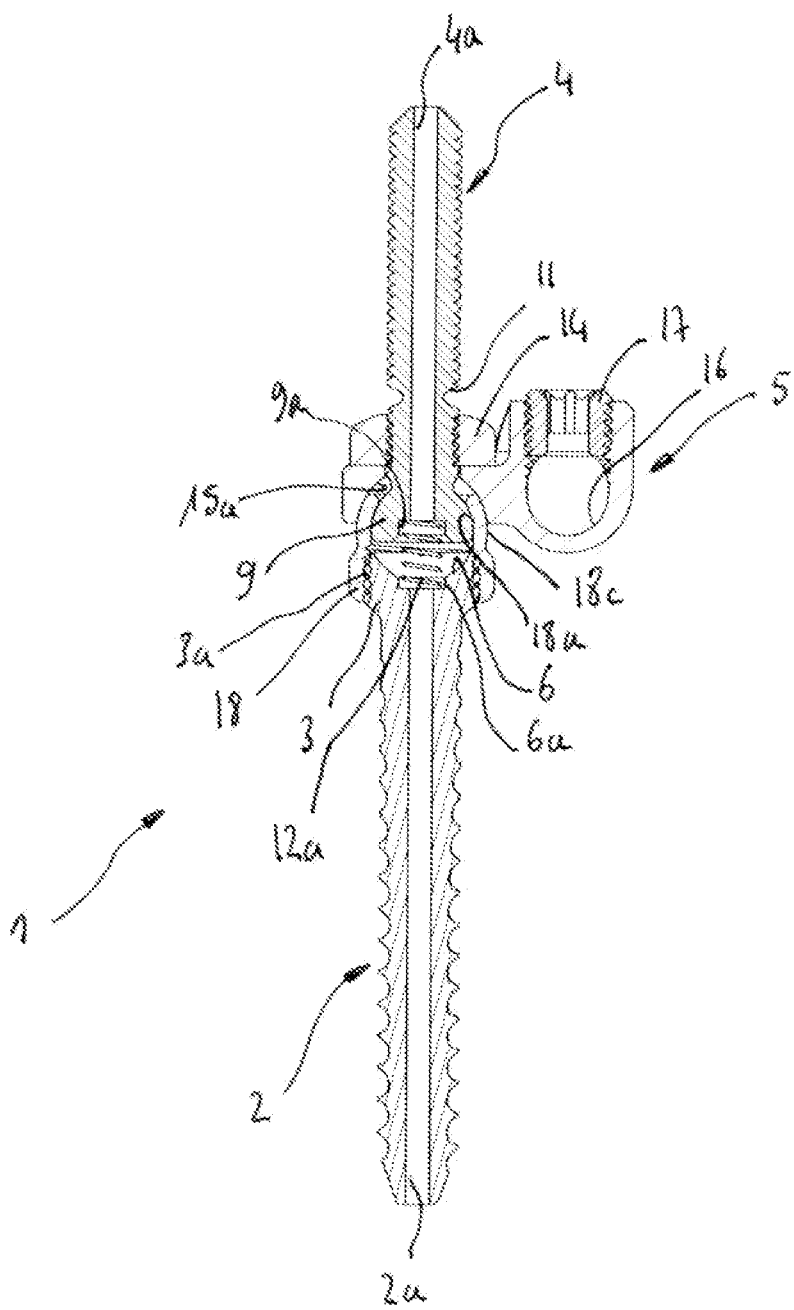
Figure 6:
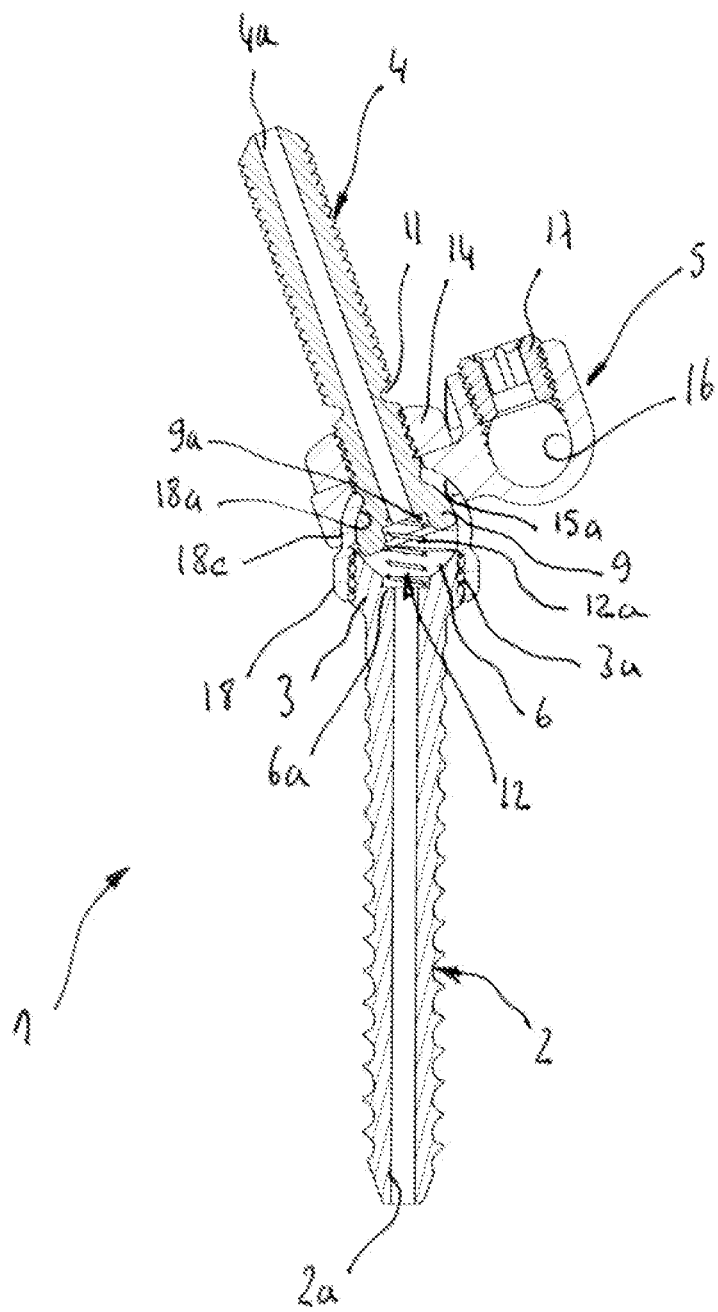

FIGS. 4 to 6 show an alternative embodiment of the polyaxial screw 1 including a threaded bone anchoring portion 2 and an anchoring portion with a mechanical thread 4 respectively provided with a head 3 and 9 connected to each other by retaining means 18 guaranteeing that said mechanical thread anchoring portion 4 has a predetermined angular position so as to be able to immobilize a linking connector 5 for a spinal fastening device thereon.

An inner housing 6 with a spherical profile is formed inside the head 3 of the threaded bone anchoring portion 2. The body of the threaded bone anchoring portion 2 is pierced in the middle thereof with a bore 2a emerging at each end of said portion.

The bore 2a emerges in a cylindrical cavity 6a formed in the bottom and middle of the inner housing 6 and whereof the inner diameter is larger than that of said bore.

The cylindrical cavity 6a is provided to receive one of the ends of the spring-shaped spiral wire 12a of the friction means 12.

The head 3 of the threaded bone anchoring portion 2 has a thread 3a on its outer face on which the retaining means 18 are screwed, making it possible, during mounting of the polyaxial screw 1, to join said threaded bone anchoring 2 and mechanical thread 4 portions to each other.

The retaining means are made up of a linking nut 18 including an opening 18b that is passed through by the mechanical thread anchoring portion 4 allowing said mechanical thread anchoring portion 4 to be able to pivot around said primary and vertical axis xx' when the polyaxial thread 1 is assembled.

The mechanical thread anchoring portion 4 is provided at one end thereof with a head 9 with a spherical outer profile. The body of the mechanical thread anchoring portion 4 is pierced in the middle thereof with a bore 4a emerging at each end of said portion.

The bore 4a emerges in a cylindrical cavity 9a formed in the head 9 and the inner diameter of which is larger than that of said bore.

The cylindrical cavity 9a is provided to receive the other end of the spring-shaped spiral thread 12a of the friction means 12 when the heads 3 and 9 are assembled using the linking nut 18.

In fact, the linking nut 18 includes an inner face 18a whereof the profile has a shape complementary to the spherical outer profile of the head 9 of the mechanical thread anchoring portion 4.

The assembly of the polyaxial screw 1, and more particularly the threaded bone anchoring portion 2 with the mechanical thread anchoring portion 4, is done as follows:

the linking nut 18 is placed around the head 9 of the anchoring portion with a mechanical thread 4 such that the inner face 18a is in contact with the outer spherical portion of said head 9;

the friction means 12, and more particularly the ends of the spring-shaped spiral wire 12a, are respectively placed in the corresponding cylindrical cavity 6a, 9a of the heads 3 and 9 during tightening of the linking nut 18 around said head 3 of the threaded bone anchoring portion bone anchoring portion [sic] 2.

It will be noted that the complete tightening of the linking nut 18 on the head 3 of the threaded bone anchoring portion 2 makes it possible to compress the spring-shaped spiral wire 12a of the friction means 12, causing the head 9 to push on the inner face 18a of said linking nut 18.

This thrust force ensures a frictional stress of the head 9 against the inner face 18a of the linking nut 18 while guaranteeing that the anchoring portion with the mechanical thread 4 is free to move in vertical translation and angular pivoting with respect to said threaded bone anchoring portion 2 when it is implanted in the vertebral body of a vertebra.

The spherical outer diameter of the head 9 of the mechanical thread anchoring portion 4 is provided with smaller dimensions than the inner dimension of the spherical housing 6 of the threaded bone anchoring portion 2, allowing guiding during angular movements of the mechanical thread anchoring portion 4 with respect to said threaded bone anchoring portion 2 of the polyaxial screw 1.

It will be noted that the linking connector 5 may be made up on the one hand of a first bore 15 passed through by the mechanical thread anchoring portion 4 of the polyaxial screw 1 and on the other hand by a second bore 16 perpendicular to the first for the passage of a link rod (not shown) that is immobilized in rotation and translation inside said second bore 16 by a set screw 17.

The nut 18 includes an outer profile 18c in the form of a sphere portion designed to cooperate with a housing 15a with a complementary profile formed at one of the ends of the first bore 15 of the connector 5 and passed through by the anchoring portion with the mechanical thread 4 of the polyaxial screw 1.

This arrangement makes it possible to guarantee, during the angular adjustment of the mechanical thread anchoring portion 4 with respect to the threaded bone anchoring portion 2, axial guidance of the linking connector 5 with respect to the angular position of said mechanical thread anchoring portion 4.

Figure 7:
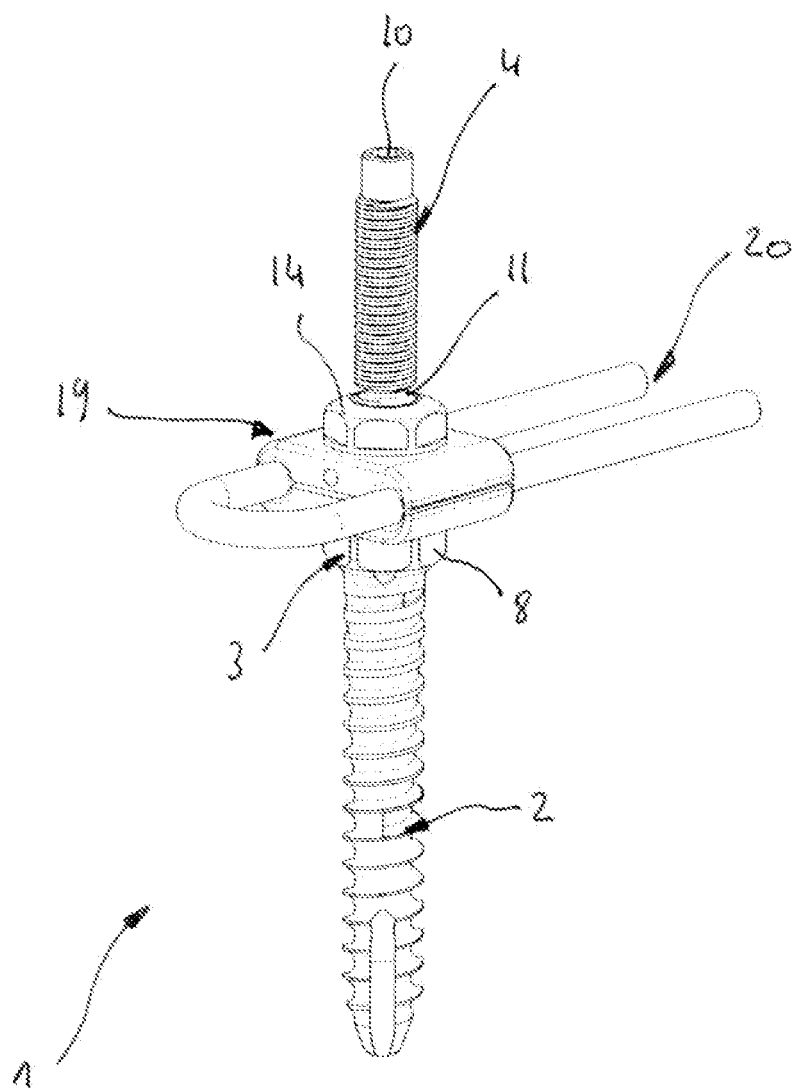
FIG. 7 is a view illustrating one example assembly of the polyaxial screw with a mechanical thread according to the present invention with a connector.

FIG. 7 shows another mounting example of the polyaxial screw 1 according to the present invention with a connector 19 with a double linking rod 20. The connector 19 replaces the connector 5 such that the tightening nut 14 cooperates with the mechanical thread anchoring portion 4.

It must also be understood that the preceding description has been provided solely as an example and that it in no way limits the scope of the invention; it would not be beyond the scope of the invention to replace the described details of the embodiments with any equivalents.

The invention claimed is:

1. A polyaxial screw, comprising:
a threaded bone anchoring portion with a first end provided with a first head;
a mechanical threaded anchoring portion with a first end provided with a second head;
retaining means connecting the first and second heads; and
friction means positioned between the first and second heads,
wherein the retaining means i) ensures that the threaded bone anchoring portion and the mechanical threaded anchoring portion cannot separate from each other while ii) guaranteeing that the mechanical threaded anchoring portion is free to move in vertical translation and angularly pivot with respect to said threaded bone anchoring portion, so as to be able to axially pre-position said mechanical thread anchoring portion with respect to an axial anchoring position of the threaded bone anchoring portion,
wherein the first head has, on an outer face thereof, a thread, and
wherein the retaining means is threaded onto the thread on the outer face of the first head ensuring that the thread bone anchoring portion and the mechanical threaded anchoring portion cannot separate from each other while guaranteeing that the mechanical thread anchoring portion is free to move in vertical translation and angularly pivot with respect to said threaded bone anchoring portion.

2. The polyaxial screw according to claim 1, wherein,
the first head of the threaded bone anchoring portion includes a housing with an interior surface,
the second head of the mechanical thread anchoring portion has a spherical outer profile with an exterior surface,
the spherical outer profile of the second head bears on the interior surface of the housing of the first head, and
the friction means are made up of a spiral wire in the form of a spring positioned against the interior surface of the housing of the first head of the threaded bone anchoring portion and against the exterior surface of the second head of the mechanical thread anchoring portion.

3. The polyaxial screw according to claim 1, wherein the mechanical thread anchoring portion is sectile.

4. The polyaxial screw according to claim 1, wherein the mechanical thread anchoring portion comprises a cavity for inserting a tool across from the second head.

5. The polyaxial screw according to claim 2, wherein the spiral wire is made from a material with a high friction coefficient.

6. The polyaxial screw according to claim 1, wherein a housing formed inside the first head of the threaded bone anchoring portion has a spherical profile.

7. The polyaxial screw according to claim 1, wherein an outer face of the first head of the threaded bone anchoring portion has cavities for placing a tool to rotate said threaded bone anchoring portion.

8. The polyaxial screw according to claim 6, wherein,
the friction means is a spring-shaped spiral wire, and
the housing formed inside the first head of the threaded bone anchoring portion includes a cylindrical cavity in a middle thereof, and
one end of the spring-shaped spiral wire is located in the cylindrical cavity.

9. The polyaxial screw according to claim 2, wherein,
the second head of the mechanical thread anchoring portion comprises a cylindrical cavity in the middle thereof,
the friction means is a spring-shaped spiral wire, and
one end of the spring-shaped spiral wire is located in the cylindrical cavity.

10. The polyaxial screw according to claim 6, wherein the retaining means is a nut including a spherical inner face cooperating with the spherical outer profile of the second head of the mechanical thread anchoring portion and a spherical outer face for receiving a linking connector of a spinal fastening device.

11. The polyaxial screw according to claim 8, wherein the retaining means is a nut including a spherical inner face cooperating with the spherical outer profile of the second head of the mechanical thread anchoring portion and a spherical outer face for receiving a linking connector of a spinal fastening device.

12. The polyaxial screw according to claim 2, wherein the spiral wire is made from an alloy of titanium or cobalt.

13. The polyaxial screw according to claim 1, wherein,
the first head of the threaded bone anchoring portion includes a housing with an interior surface having a spherical profile and a cylindrical cavity in a middle of the interior surface,
the second head of the mechanical thread anchoring portion has a spherical outer profile with an exterior surface,
the spherical outer profile of the second head bears on the interior surface of the housing of the first head,
the friction means is a spring with i) a first end positioned in the cylindrical cavity of the housing formed inside the first head of the threaded bone anchoring portion and ii) a second end positioned against the exterior surface of the second head of the mechanical thread anchoring portion,
the retaining means is a nut threaded onto the thread on the outer face of the first head ensuring that the thread-bond anchoring portion and the mechanical threaded anchoring portion cannot separate from each other while guaranteeing that the mechanical thread anchoring portion is free to move in vertical translation and angularly pivot with respect to said threaded bone anchoring portion,
the nut includes an upper portion with i) a spherical inner face cooperating with the spherical outer profile of the second head of the mechanical thread anchoring portion, and ii) a spherical outer face for receiving a linking connector of a spinal fastening device,
the mechanical thread anchoring portion is sectile, and
a second end of the mechanical thread anchoring portion, opposite the first end of the mechanical thread anchoring portion, comprises a cavity for inserting a tool across from the second head.

14. The polyaxial screw according to claim 1, wherein,
the first head of the threaded bone anchoring portion includes a housing with an interior surface,
the second head of the mechanical thread anchoring portion has an exterior surface,
the exterior surface of the second head bears on the interior surface of the housing of the first head,
the friction means is a spring with i) a first end positioned in the housing formed inside the first head, and ii) a second end positioned against the exterior the mechanical thread anchoring portion,
the retaining means is a nut threaded onto the thread on the outer face of the first head, ensuring that the thread-bond anchoring portion and the mechanical threaded anchoring portion cannot separate from each other while guaranteeing that the mechanical thread anchoring portion is free to move in vertical translation and angularly pivot with respect to said threaded bone anchoring portion,
the nut includes an upper portion with i) a spherical inner face cooperating with the spherical outer profile of the second head of the mechanical thread anchoring portion, and ii) a spherical outer face for receiving a linking connector of a spinal fastening device,
the mechanical thread anchoring portion is sectile, and
a second end of the mechanical thread anchoring portion, opposite the first end of the mechanical thread anchoring portion, comprises a cavity for inserting a tool across from the second head.

15. The polyaxial screw according to claim 13, wherein the spiral wire is made from an alloy of titanium or cobalt.

* * * * *